United States Patent
Tomatsu

[11] Patent Number: 5,993,486
[45] Date of Patent: Nov. 30, 1999

[54] ARTIFICIAL LIGAMENT

[75] Inventor: Taisuke Tomatsu, Kawasaki, Japan

[73] Assignee: Senko Medical Instrument Mfg. Co., Ltd., Japan

[21] Appl. No.: 09/128,417

[22] Filed: Aug. 4, 1998

[30] Foreign Application Priority Data

Sep. 18, 1997 [JP] Japan .................................. 9-253927

[51] Int. Cl.$^6$ .............................. A61F 2/08; A61F 2/30
[52] U.S. Cl. ............................................... 623/13; 623/18
[58] Field of Search ................................. 623/13, 11, 16, 623/18, 21, 61

[56] References Cited

U.S. PATENT DOCUMENTS

| | | | |
|---|---|---|---|
| 3,979,779 | 9/1976 | Zeibig et al. | 3/1.91 |
| 4,632,100 | 12/1986 | Somers et al. | 128/92 |
| 5,002,574 | 3/1991 | May et al. | 623/13 |
| 5,151,104 | 9/1992 | Kenna | 606/73 |
| 5,395,370 | 3/1995 | Muller et al. | 606/61 |
| 5,507,812 | 4/1996 | Moore | 623/13 |
| 5,702,389 | 12/1997 | Taylor et al. | 606/54 |

*Primary Examiner*—David H. Willse
*Assistant Examiner*—Alvin Stewart
*Attorney, Agent, or Firm*—Parkhurst & Wendel, LLP

[57] ABSTRACT

An artificial ligament 12 comprises a ligament section 12 having a long narrow shape, and coupling sections provided on both ends. The coupling sections comprise balls which are fixed at both ends of the ligament section, and holding body in which a holding space is formed within the inner section by means of cap section covering the holding body base section so as to hold the balls in a slidable manner. Attachment holes are formed in the bones of the joint, and the coupling sections are fixed by being screwed into the attachment holes. After transplantation of this ligament, there is no damage to the artificial ligament when the joint is extended, and long lasting use can be expected.

9 Claims, 5 Drawing Sheets

ARTIFICIAL LIGAMENT

BACKGROUND OF THE INVENTION

1. Field of the Invention

The present invention relates to an artificial ligament for transplantation to a joint such as the knee, ankle, or elbow which has lost its ligament.

2. Description of the Related Art

For athletes who participate in sports such as soccer, rugby and skiing in which movement is very intense, injuries to the ligaments of joints such as the knee, ankle, or elbow are numerous. In particular, when these ligaments are severed, transplantation of artificially made ligament or ligament taken from a living body is carried out for strengthening purposes and the like.

When these types of artificial ligament are transplanted, as shown in FIG. 7, firstly, holes 2 for attaching an artificial ligament 1 are formed in the vicinity of the joint of bones B which are to be connected by means of the artificial ligament 1, the artificial ligament 1 is inserted through these holes 2, and both ends thereof are fixed to bones B by means of staples 3.

However, when an artificial ligament 1 is transplanted in the above way, for example, the artificial ligament 1 makes contact with and rubs on the peripheral section 2a of the opening of holes 2 formed in bones B for the purpose of attachment, and there is concern that the artificial ligament 1 will be damaged due to this friction. In addition, there is the problem that, due to repetitive bending of the artificial ligament 1 at these peripheral sections 2a of the openings, stress is exerted on the artificial ligament 1 at these sections and damage of the artificial ligament is promoted.

Consequently, it is an object of the present invention to provide an artificial ligament which, after transplantation, is long lasting and does not become damaged even by extension of the joint.

SUMMARY OF THE INVENTION

The artificial ligament of the present invention is an artificial ligament which is arranged extending between the bones which make up a joint, and comprises a ligament section formed in a long narrow shape, and coupling sections provided on both ends of the above mentioned ligament section which are respectively attached to the above-mentioned bones.

Consequently, since the coupling sections are respectively attached to the bones, even if the ligament sections are pulled in various directions due to extension of the joint, there is no contact between the ligament and the peripheral section of the opening of the holes in the bones in contrast to the structure in which the ligament is fixed by staples and passes through the holes formed in the bone. Therefore, it is possible to actually prevent damage to the ligament section due to rubbing with the peripheral section of the opening, and it is possible to anticipate long lasting use.

BRIEF DESCRIPTION OF THE INVENTION

DETAILED DESCRIPTION OF THE PREFERRED EMBODIMENTS OF THE PRESENT INVENTION

In the following, embodiments of the artificial ligament of the present invention will be explained with reference to the drawings.

Figure 1:
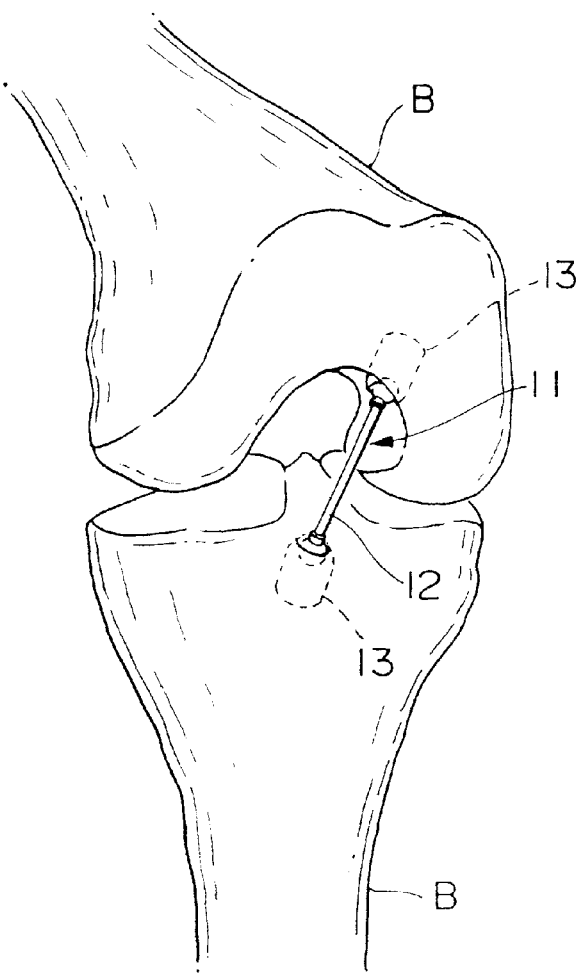
FIG. 1 is an outline side view diagram of an affected part provided with an artificial ligament for explaining the construction and composition of the artificial ligament of the present invention.

In FIG. 1, reference 11 is an artificial ligament. This artificial ligament 11 comprises a long narrow ligament section 12 comprising an artificially made ligament or a ligament taken from a living body, and a coupling section 13 provided at each end of the ligament section 12.

Figure 3:
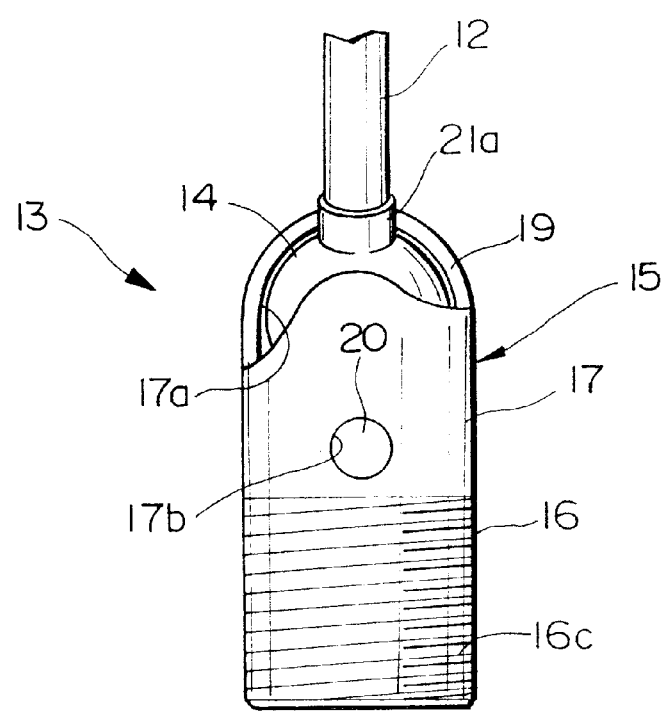
FIG. 3 is a side view of the coupling section for explaining the construction and composition of the artificial ligament of the present invention.
Figure 2:
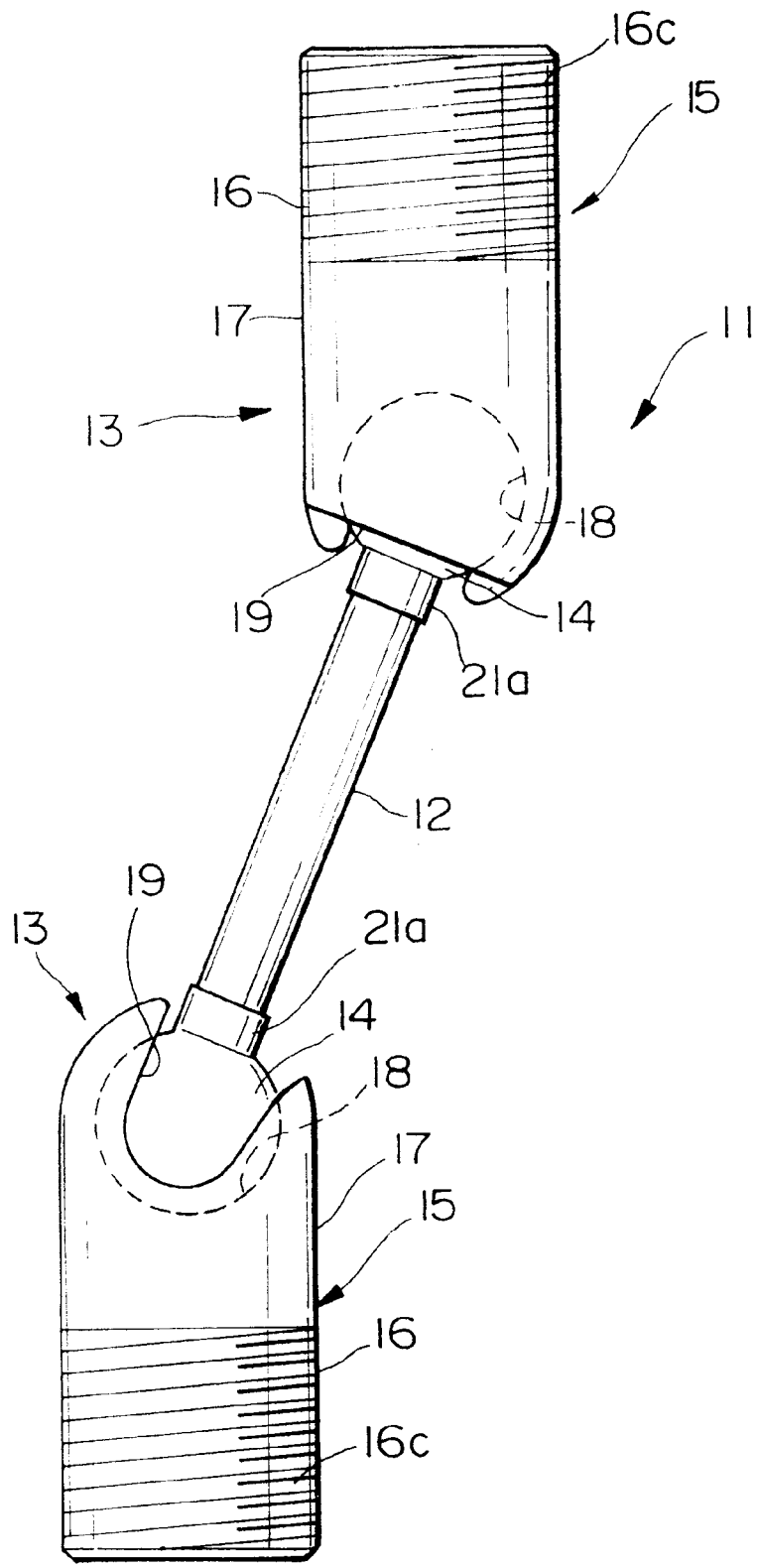
FIG. 2 is a side view of the artificial ligament for explaining the construction and composition of the artificial ligament of the present invention.
Figure 4:
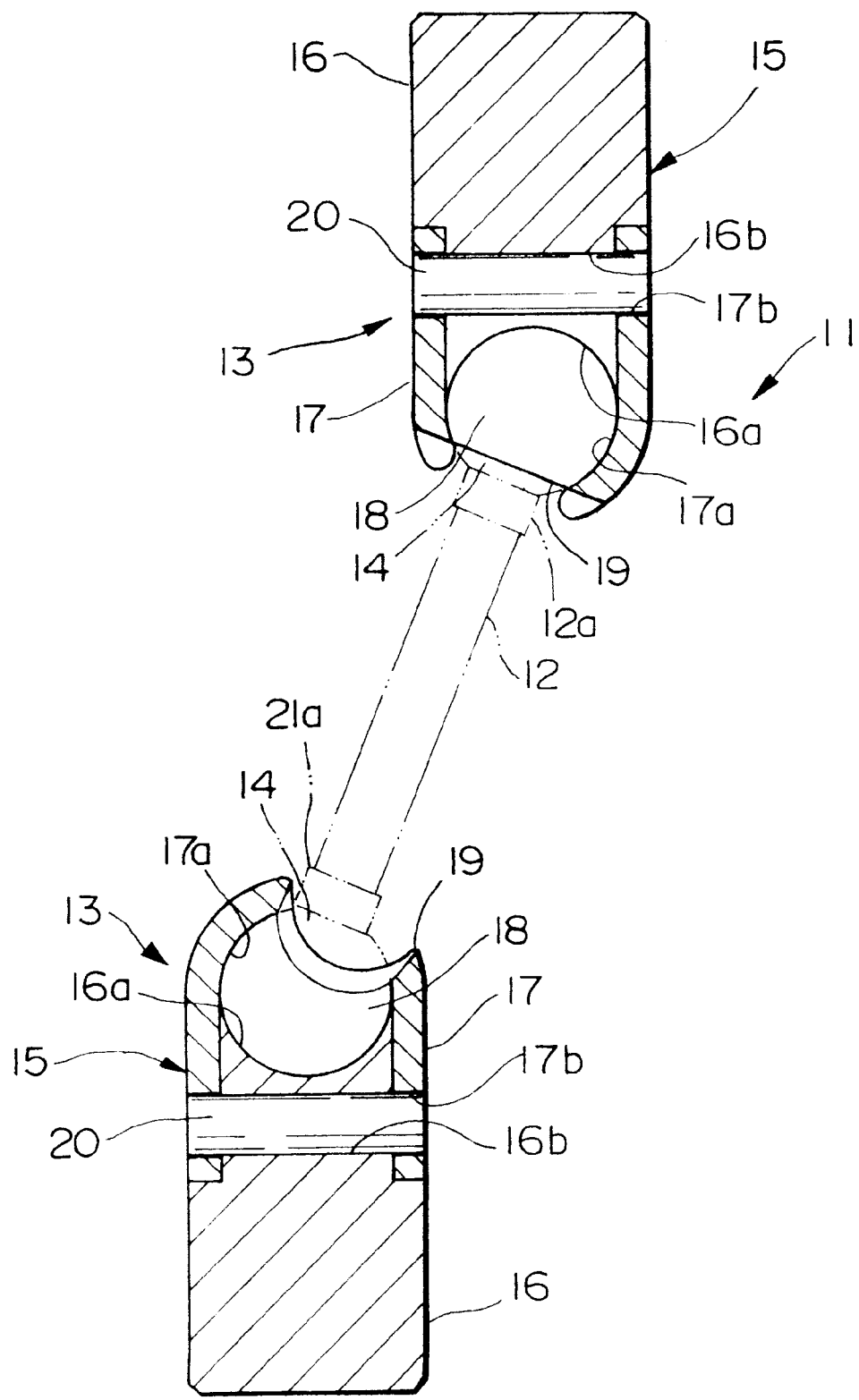
FIG. 4 is a cross-section of the artificial ligament for explaining the construction and composition of the artificial ligament of the present invention.

As shown in FIG. 2 to FIG. 4, the coupling section 13 comprises balls 14 which are fixed to both ends of the ligament section 12, and holding bodies 15 which hold these balls 14. These balls 14 are held by holding body 15 in such a manner that they can slide in all directions.

The holding body 15 comprises a holding body base section 16 which has a concave section 16a having a spherical shape formed in the upper section thereof, and a cap section 17 which has a concave surface 17a having a spherical shape formed in the inner surface thereof. This cap section 17 is attached covering the upper section of the above-mentioned holding body base section 16. Then, by means of the attachment of this cap section 17 to the holding body base section 16, a holding space 18 which holds the above-mentioned ball 14 is formed by means of the concave section 16a of holding body base section 16 and the concave surface 17a of the cap section 17. In addition, a window section 19 is formed in the cap section 17, and ligament section 12 is inserted through this window section 19.

In more detail, in the coupling section 13, because the balls 14 which are provided at both ends of the ligament section 12 can be slidably moved in all directions within the holding space of the holding body 15, the place of connection of the ligament section 12 and the ball 14 is such that movement in all directions within the range of the window section 19 which is formed in the cap 17 is possible. In addition, in the holding body base section 16 and the cap section 17 which form holding body 15, communicating apertures 16b and 17b are formed which mutually communicate when covered by cap section 17. A connecting pin 20 is inserted through these connecting apertures 16b and 17b. Then, holding body base section 16 and cap section 17 are mutually connected by this connecting pin 20.

In addition, a male screw 16C is formed in the periphery of holding body base section 16. By means of screwing this holding body base section 16 into the attachment hole formed in bone B, the holding body base section 16 becomes firmly fixed in bone B.

In addition, as the above mentioned holding body 15 and the ball 14 which make up the above mentioned coupling section 13, for example, cobalt chrome, titanium, ceramic, or the like can be used.

Figure 5:
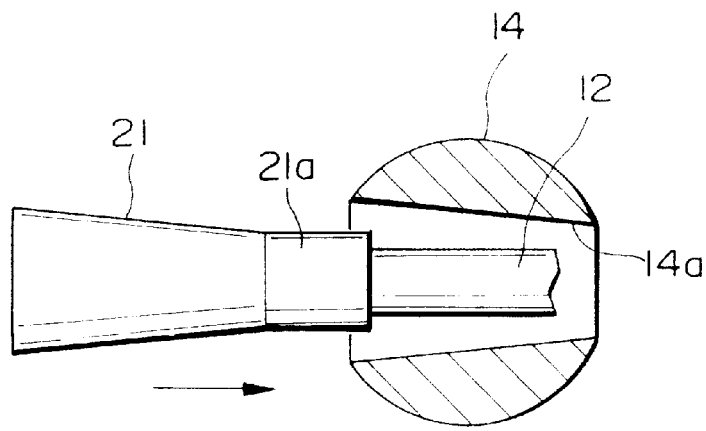
FIG. 5 is a cross-section for explaining the construction of the end sections of the artificial ligament for explaining the construction and composition of the artificial ligament of the present invention.
Figure 7:
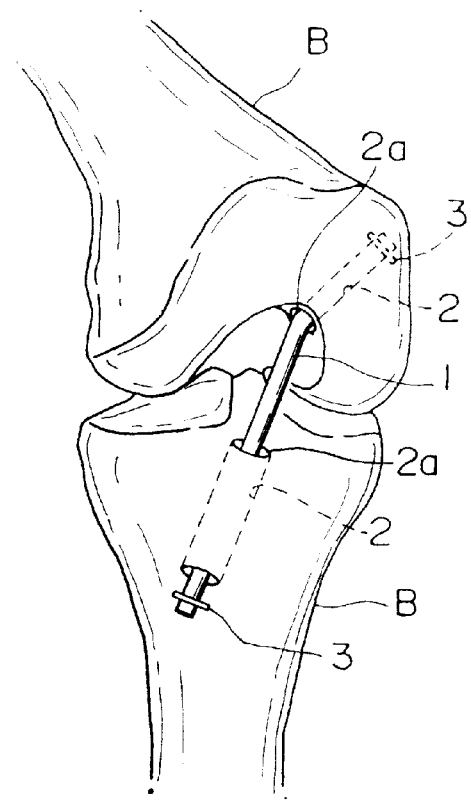
FIG. 7 is an outline side view of an affected part provided with an artificial ligament for explaining the structure of the conventional attachment of an artificial ligament.

Furthermore, as shown in FIG. 5, wedge members 21 are fixed at both ends of ligament section 12. Balls 14 are fixed to the ends of ligament section 12 by means of the insertion of wedge members 21 into tapered holes 14a formed in balls 14. In addition, in the tips of these wedge members 21, protection sections 21a are formed. By means of these protection sections 21a, when the balls 14 rotate within holding body 15, these protection sections 21a come into contact with the edges of window section 19 of the above-mentioned cap section 17. In other words, the edge section of the window sections 19 of this cap section 17 do not come into direct contact with ligament section 12.

In addition, when an artificial ligament 11 having the above-described structure is fitted to the effected section of a patient, first, respective attachment holes are formed in the bones B of the joint to which this artificial ligament is to be attached, and a female screw thread is formed in the inner surface of these attachment holes.

Next, into these attachment holes in which female screw threads have been formed, the holding body 15 which makes up the coupling section 13 of the artificial ligament 11 is attached by means of screwing the male screw 16c formed in the periphery of the holding body base section 16 into the female screw thread of the attachment hole.

When this is done, the holding bodies 15 are screwed into and fixed in the attachment holes formed in bones B.

In this way, by means of anchoring holding sections 15 in each of the attachment holes formed in bones B, the ligament section 12 is fixed in a condition in which it is arranged extending between each of bones B.

Therefore, when the patient extends the joint, this ligament section 12 can be pulled in all directions involved in that movement. In addition, in this way, when the ligament section 12 is pulled in each direction, in the coupling sections 13, the balls 14 which are held within the holding bodies 15 slide within holding spaces 18 of holding bodies 15, and, within the window sections 19 of the cap sections 17 of the holding bodies 15, the connecting place of the balls 14 with the ligament sections 12, in other words, the protecting sections 21a formed in the vicinity of both ends of ligament section 12, move according to the pulling direction of the ligament section 12.

In other words, there is no excessive twisting and the like produced at both ends of the ligament section 12 and, therefore, damage of the ends of the ligament section 12 can be prevented with certainty. In addition, when compared with the situation in which the ligament is attached by means of the ligament being passed through a hole formed in the bones and then stapled, since there is no contact between the ligament section 12 and the periphery of the opening of the attachment hole of bone B, damage to the ligament section 12 due to rubbing with the periphery of the opening can be prevented with certainty and it is possible to plan for long lasting use.

Moreover, as the attachment structure to bone B of holding body 15 which makes up coupling section 13, in the above-described example, a female screw thread is formed in the inner surface of the attachment hole formed in bone B, and a male screw 16c formed in the periphery of the holding body base section 16 of holding body 15 is screwed in. However, any attachment structure is suitable if the attachment structure is able to provide attachment to bone B which is reliable. For example, attachment by means of forming a simple attachment hole in bone B and screwing holding body 15 into this attachment hole is also suitable.

In addition, the attachment structure of the balls 14 to each end of the ligament section 12 is not limited to the above-described example, and, for example, it is also suitable for the balls 14 to be fixed to both ends of the ligament section 12 by means of passing the ligament section 12 through taper hole 14a of ball 14 and forming a knot therein, then fitting the knot into this taper hole 14a.

Figure 6:
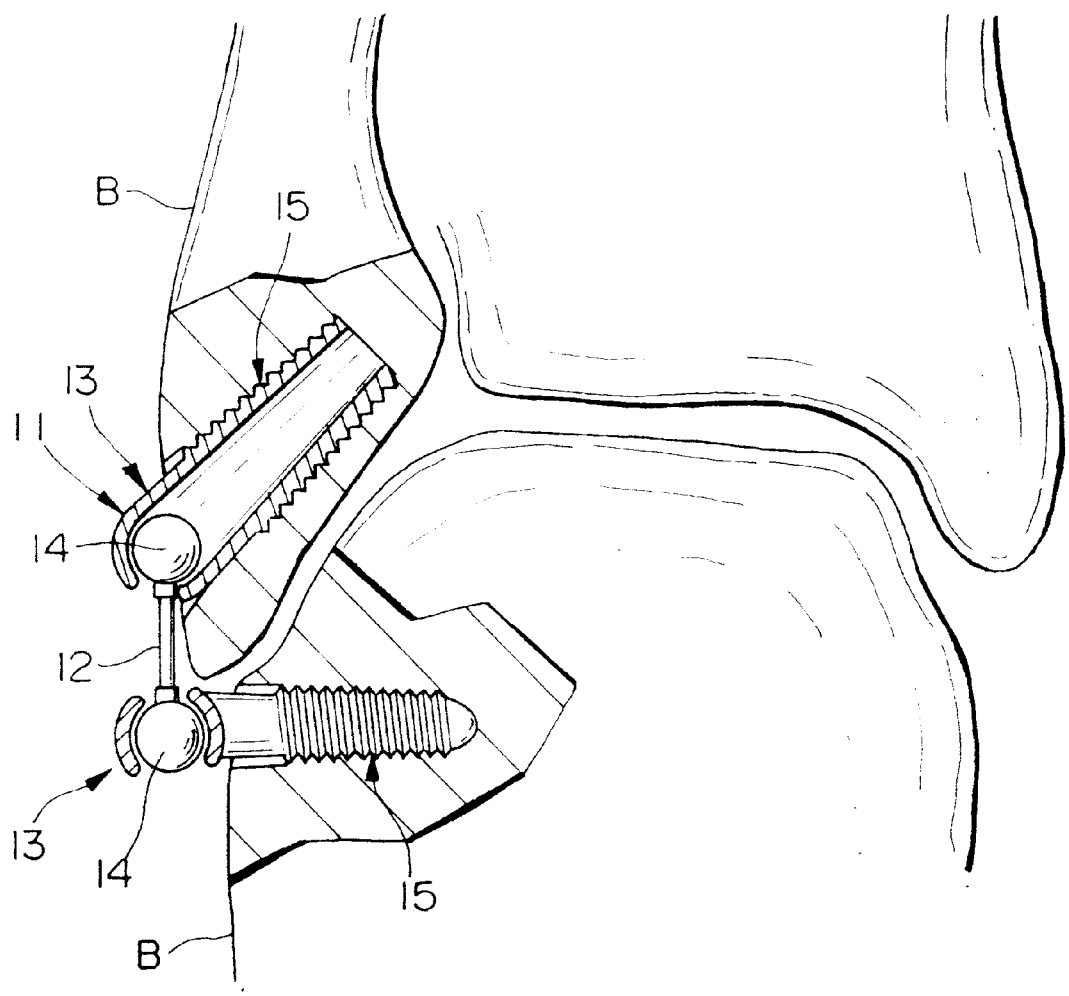
FIG. 6 is an outline side view with a cut away section of the knee joint of a patient equipped with an artificial ligament.

Furthermore, this artificial ligament 1 1 can naturally be used in any joint. With regard to this, FIG. 6 shows an example of the use of artificial ligament 11 as the medial ligament of the knee joint. Moreover, in this example, unitarily formed holding bodies 15 having peripheries which have been formed as male screws are used, and these holding bodies 15 are attached by means of being screwed into the attachment hole which was formed in advance in bone B.

What is claimed is:

1. An artificial ligament for arrangement extending between bones which form a joint comprising:
    a ligament section having a long narrow shape and two ends;
    a coupling section provided on each end of said ligament section which coupling sections are adapted to be respectively attached to said bones, wherein each coupling section comprises a ball fixed to an end of said ligament section, a holding body forming a holding space for receiving said ball in a slidable manner, and a tapered hole formed in each ball, said ligament section passing through said tapered hole, and a wedge member fixed to an end of said ligament engaged in said tapered hole.

2. An artificial ligament according to claim 1, wherein a male screw is formed on a holding body for screwing into said bone.

3. An artificial ligament according to claim 1, wherein a protecting section for preventing said ligament from making contact with one of said holding bodies of the ligament section is formed on said wedge member.

4. An artificial ligament according to claim 1, wherein at least one of said holding bodies and at least one of said balls comprise cobalt chrome.

5. An artificial ligament according to claim 1, wherein at least one of said holding bodies and at least one of said balls comprise titanium.

6. An artificial ligament according to claim 1, wherein at least one of said holding bodies and at least one of said balls comprise ceramic material.

7. An artificial ligament according to claim 1, wherein at least one of said holding bodies comprises:

a holding body base section having a concave section having a spherical shape formed in an upper section thereof; and a cap section in which a concave surface having a spherical shape is formed in an inner surface thereof, wherein this cap is attached covering said upper section of said holding body base section and thereby a holding space is formed in which said ball is held by means of the concave section of the holding body base section and the concave surface of said cap.

8. An artificial ligament according to claim 7, wherein a window section is formed in said cap and said ligament section passes through said window section.

9. An artificial ligament according to claim 7, wherein communicating apertures are formed in said holding body base section and said cap, and when the holding body base section is covered by the cap section, a connecting pin is inserted through said communicating apertures, thereby said holding body base section and said cap section are mutually connected.

\* \* \* \* \*